Feb. 2, 1954 F. W. ANDERSON Plant Pat. 1,249
NECTARINE TREE
Filed March 17, 1953
Fig. 1
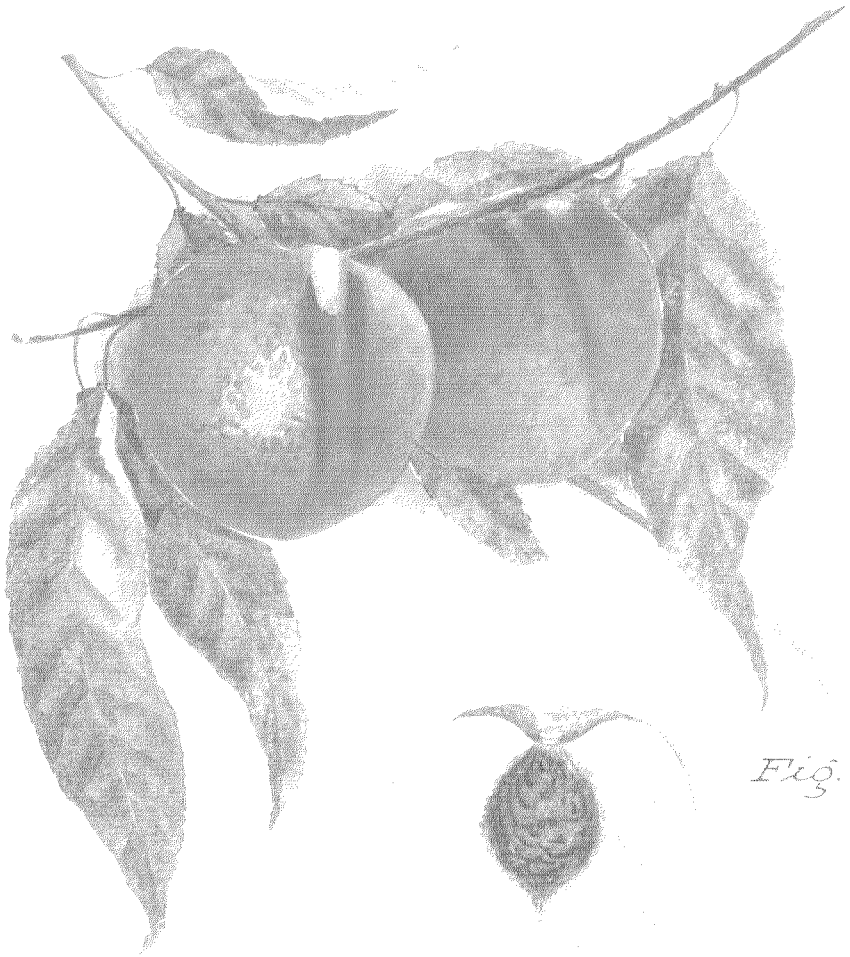
Fig. 2
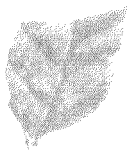
Fig. 3
WITNESS
Addison F. Avery
INVENTOR
Frederic W. Anderson
ATTYS Patented Feb. 2, 1954

Plant Pat. 1,249

UNITED STATES PATENT OFFICE 1,249

NECTARINE TREE

Frederic W. Anderson, Merced, Calif.

Application March 17, 1953, Serial No. 343,007

1 Claim. (Cl. 47—62)

The present invention is directed to a new and distinct variety of nectarine tree which bears yellow fleshed, freestone fruit.

For a number of years I have conducted an extensive plant breeding program for the origination of commercially desirable nectarine trees; this program having been carried out in my experimental nursery and orchard near Le Grand, Merced County, California.

One of the primary aims of such program has been the origination of a series of new and distinct nectarine varieties having different ripening periods, but which periods are sufficiently related that a relatively long harvest season of nectarine fruit may be attained by the planting of a number of such varieties.

An additional aim of such program has been, with respect to the instant variety, to provide a freestone nectarine available to the market at approximately the same time as early peaches.

As compared with the John Rivers nectarine (unpatented), which is widely grown in California, the present variety of nectarine tree bears fruit which has yellow instead of white flesh; ripens about one week later; is slightly larger; has more red exterior color; has firmer flesh; has a shorter chilling requirement; is a much heavier and more regular producer; and is a freestone instead of a semi-clingstone.

As compared to the Sun Grand variety of nectarine (United States Plant Patent 974), the present variety has the same ancestry and resembles it rather closely in physical characteristics, except that the fruit is smaller and ripens about ten days to two weeks earlier; the harvest being complete before the beginning of harvest of such Sun Grand variety of nectarine.

In 1952 the dates of the first and last picking of the fruit of the present variety were June 28th and July 6th respectively, whereas picking of the John Rivers nectarine began on June 23rd and concluded on June 30th.

By further comparison, picking of the Sun Grand nectarine began on July 7th and concluded on July 17th, 1952.

The new and distinct variety of nectarine tree here claimed was developed and asexually reproduced by me in my experimental nursery and orchard near Le Grand, County of Merced, California, in the following manner:

The variety is a second generation cross of Kim nectarine (United States Plant Patent No. 173) crossed with the July Elberta peach (United States Plant Patent No. 15). The first generation of this cross consisted of a group of yellow-fleshed peaches. When the seeds of these peaches were planted the resulting progeny proved to be approximately three-fourths peaches and one-fourth nectarines. As soon as these trees had blossoms, the peaches were eliminated and the nectarines permitted to fruit for further observation and recording. Among these nectarine trees the instant variety was the earliest to ripen, being from ten days to two weeks earlier than the Sun Grand variety, which was a result of the same cross.

Subsequent to its discovery the present variety of nectarine tree has been top-worked—on a number of occasions—onto mature root stock in my identified orchard, and such asexual reproductions have, in each instance, run true in all respects.

In the original drawings:

Fig. 1 is an elevation of two of the fruit of the present variety, together with twigs and leaves.

Fig. 2 is a sectional elevation of one of the fruit with the stone exposed.

Fig. 3 is a fragmentary elevation taken from the top side of one of the leaves.

Referring now more specifically to the pomological details of this new and distinct variety of nectarine tree, the following is an outline description thereof; all major color plate identifications being by reference to Maerz and Paul Dictionary of Color:

Tree: Large size; medium strength; spreading; dense; vase formed; productive; regular bearer.
Trunk: Medium size; medium texture.
Branches: Medium size; medium texture.
*Color.*—Brown.
*Lenticels.*—Medium number; medium size.
Leaves: Large size. Average length, 6½ inches; average width, 2 inches. Thick.
*Color.*—Top side—medium green (22–L–7); under side—light green (22–K–6).
*Margin.*—Crenate.
*Petiole.*—Medium length.
*Glands.*—Average number—four. Alternate; medium size; globose; positioned mostly on blade, occasionally on petiole. Stipules—none.
Flower buds: Medium size; plump.
Flowers: Large size; medium blooming period; first and full bloom with Elberta peach.
Fruit: Maturity when described—hard—June 30, 1952.
*Size.*—Medium; uniform. Average diameter axially, 2¼ inches; average transverse in suture plane, 2½ inches.

*Form.*—Uniform; symmetrical.
*Suture.*—A distinct line extending from base to beyond apex, with slight depression beyond pistil point.
*Ventral surface.*—Rounded slightly.
*Lips.*—Equal.
*Cavity.*—Rounded.
*Apex.*—Short.

Skin: Thick; tough.
*Tendency to crack.*—None.
*Down.*—Wanting.
*Color.*—Yellow (11–L–7) almost completely overlaid with orange red (5–L–5), mottled and streaked deeper red (6–L–6).

Flesh:
*Color.*—Yellow (9–L–4, shading to 9–L–6), with red (3–L–8) near stone.
*Surface of pit cavity.*—Pink.
*Amygadalin.*—Moderate.
*Juice.*—Moderate.
*Texture.*—Firm; meaty.
*Fibres.*—Few.
*Ripens.*—Evenly.
*Flavor.*—Vinous.
*Aroma.*—Distinct.
*Eating quality.*—Good to best.

Stone: Free; parts from flesh smoothly.
*Size.*—Medium. Average length, 1¼ inches; average breadth, 11/16 inch; average thickness, ½ inch.

*Form.*—Oval.
*Base.*—Oblique.
*Hilum.*—Oval.
*Apex.*—Rounded.
*Sides.*—Equal.
*Color.*—Brown (7–H–10).

Keeping quality: Good.

Use: Local; dessert; culinary; long distance shipping.

The tree and its fruit herein described may vary in slight detail due to climatic and soil conditions under which the variety may be grown.

Having thus described my invention, I claim:

A new and distinct variety of nectarine tree, as described and illustrated, bearing medium sized, firm, yellow-fleshed freestone fruit having yellow skin almost entirely overspread with red; characterized—in comparison with the John Rivers nectarine—by yellow instead of white flesh; ripening approximately one week later; slightly larger; more exterior red color; firmer fleshed; shorter chilling requirement; heavier and more regular producer; and freestone instead of semi-clingstone; and—by comparison with the Sun Grand nectarine—having general resemblance thereto but being smaller in fruit size, and ripening ten days to two weeks earlier.

FREDERIC W. ANDERSON.

No references cited.

Certificate of Correction

Patented February 2, 1954 Plant Patent No. 1,249

Frederic W. Anderson

It is hereby certified that it appears that a mistake has been made in the above numbered patent and a showing has been made that such mistake occurred in good faith and was not the fault of the Patent Office, said mistake requiring correction as follows:

Column 2, line 49, for "Large size" read *Medium size*;

and that the said patent should be read as though corrected as specified.

Signed and sealed this 18th day of May, A. D. 1954.

[SEAL]

ARTHUR W. CROCKER,
*Assistant Commissioner of Patents.*